(12) United States Patent
Hartlep et al.

(10) Patent No.: US 7,740,606 B2
(45) Date of Patent: Jun. 22, 2010

(54) METHOD AND APPARATUS FOR AUTOMATED OPTIMIZATION OF TREATMENT PLANS

(75) Inventors: Andreas Hartlep, Naring (DE); Maria Inmaculada Rodriguez Ponce, Munich (DE)

(73) Assignee: BrainLAB AG, Feldkirchen (DE)

( * ) Notice: Subject to any disclaimer, the term of this patent is extended or adjusted under 35 U.S.C. 154(b) by 804 days.

(21) Appl. No.: 11/562,272

(22) Filed: Nov. 21, 2006

(65) Prior Publication Data

US 2008/0015432 A1 Jan. 17, 2008

Related U.S. Application Data

(60) Provisional application No. 60/754,509, filed on Dec. 28, 2005.

(30) Foreign Application Priority Data

Nov. 21, 2005 (EP) .................................. 05025352

(51) Int. Cl.
*A61M 31/00* (2006.01)

(52) U.S. Cl. ...................................................... 604/67

(58) Field of Classification Search ................... 604/67; 600/407
See application file for complete search history.

(56) References Cited

U.S. PATENT DOCUMENTS

| 6,549,803 B1 | 4/2003 | Raghavan et al. |
| 2003/0114751 A1 | 6/2003 | Pedain et al. |
| 2004/0138551 A1* | 7/2004 | Hartlep et al. .............. 600/407 |

FOREIGN PATENT DOCUMENTS

EP 01 128 614.3 11/2001

OTHER PUBLICATIONS

Mardor Y. et al., "Convection-enhanced drug delivery: Increased efficacy and magnetic resonance image monitoring", Cancer Research, vol. 65, No. 15, Aug. 2005, pp. 6858-6863.

* cited by examiner

*Primary Examiner*—Nicholas D Lucchesi
*Assistant Examiner*—Diva Ranade
(74) *Attorney, Agent, or Firm*—Renner, Otto, Boisselle & Sklar, LLP

(57) ABSTRACT

A method of adjusting infusion parameters that provide coverage of a selected target volume for direct infusions of a fluid includes using an algorithm for calculation of optimal packing of spheres or cylinders in a selected volume to determine the coverage of the selected target volume.

28 Claims, 3 Drawing Sheets

METHOD AND APPARATUS FOR AUTOMATED OPTIMIZATION OF TREATMENT PLANS

RELATED APPLICATION DATA

This application claims priority of U.S. Provisional Application No. 60/754,509 filed on Dec. 28, 2005, which is incorporated herein by reference in its entirety.

FIELD OF THE INVENTION

The present invention relates to a method and apparatus for automated optimization of treatment plans and, more particularly, to the optimization of convection enhanced delivery (CED) treatment plans performed or implemented after tumor resection.

BACKGROUND OF THE INVENTION

A target area for an intra-cranial infusion is conventionally estimated by a neuro-surgeon who utilizes medical images, such as MR-images. In cases of CED treatment after tumor resection, the physician typically implements a "safety-range" of about 2 cm around the resection cavity as the infusion target and the area of T2 enhancement that is identified with potential edema. These areas are quite likely areas of remaining and/or migrating tumor cells. The physician then tries to target these areas by implementing catheters to infuse a drug according to a treatment protocol, wherein the physician may be supported by simulation predictions generated by a software application or the like.

SUMMARY OF THE INVENTION

According to one aspect of the invention, a method of adjusting infusion parameters that provide coverage of a selected target volume for direct infusions of a fluid comprises using an algorithm for calculation of optimal packing of spheres or cylinders in a selected volume to determine the coverage of the selected target volume. The fluid can be at least one of a drug, diluted cells, viral vectors, molecules, diluted microspheres, or diluted micelles. Further, the spheres or cylinders can refer to a geometrical shape of the fluid distribution.

Additionally, the geometrical shape of the fluid distribution can be calculated based on convection related parameters. Calculating the geometrical shape can include, for example, using at least one of flow rate, pressure head, infusion time, catheter radius, catheter type, tissue properties as the convention related parameters. Calculating the geometrical shape of the fluid distribution also can be based on diffusion related parameters.

Calculating the geometrical shape can include using at least one of time, diffusivity, infusion time, concentration gradients, catheter radius, infusate properties, catheter type, catheter number, tissue properties as the diffusion related properties.

The infusion parameters can include a flow rate, pressure, and/or infusion time for at least one catheter, as well as catheter types and/or catheter diameters for at least one catheter. The infusion parameters also can include a number of catheters used to perform the infusion, a position of a catheter trajectory and/or a position of a catheter tip for at least one catheters. The infusion parameters also can include or take into consideration catheter placement guidelines for at least one catheter.

The method can further include manually adjusting at least one of the parameters for at least one catheter and/or automatically calculating at least one of the parameters for at least one catheter.

Additionally, the method can include acquiring from external sources at least one of the parameters for at least one catheter. Acquiring can include using software, literature or a user as an external source.

At least one catheter can be interactively removed and the coverage of the selected target volume can be automatically updated to reflect the removal. Further, at least one parameter can be interactively removed and/or changed, and the selected target volume can be automatically updated to reflect the removal or change.

The target volume can be manually or automatically outlined, and the target volume can be rated in terms of risk structures. Additionally, at least one outlined target volume can be rated in terms of importance of its coverage or in terms of importance of avoidance of its coverage.

The method can further comprise adjusting a demanded overlap between the target volume and a calculated infusion area and/or adjusting the demanded overlap between the target volume and a calculated non-infusion area. Further, an overlap between infusion results from different catheters can be adjusted, wherein adjusting the overlap includes adjusting the overlap in terms of maximum concentration threshold.

The fluid distribution in the target volume also can be adjusted in terms of therapeutic effects.

Additionally, at least part of the determined coverage can be used to refine plans for placement of intra-cranial catheters, wherein using at least part of the determined coverage can include automatically or manually refining the plans.

A system for adjusting infusion parameters that provide coverage of a selected target volume in tissue for direct infusion of a fluid, can include: an imaging device for obtaining image data; a processor coupled to the imaging device and operative to obtain patient-specific medical and/or anatomical image data from the imaging device; a data bank coupled to the processor and including information for calculating infusion relevant parameters from the imaging data obtained from the imaging device; and an infusion system including at least one delivery device and at least one injecting mechanism, said injecting mechanism controllable by the processor based on the information obtained from the imaging device and/or the data bank so as to cover the target volume with a substance delivered or infused by the at least one delivery device, wherein the coverage of the target volume is determined by an algorithm for calculating optimal packing of spheres or cylinders in a selected volume.

BRIEF DESCRIPTION OF THE DRAWINGS

The forgoing and other features of the invention are hereinafter discussed with reference to the drawings.

DETAILED DESCRIPTION

Figure 1:
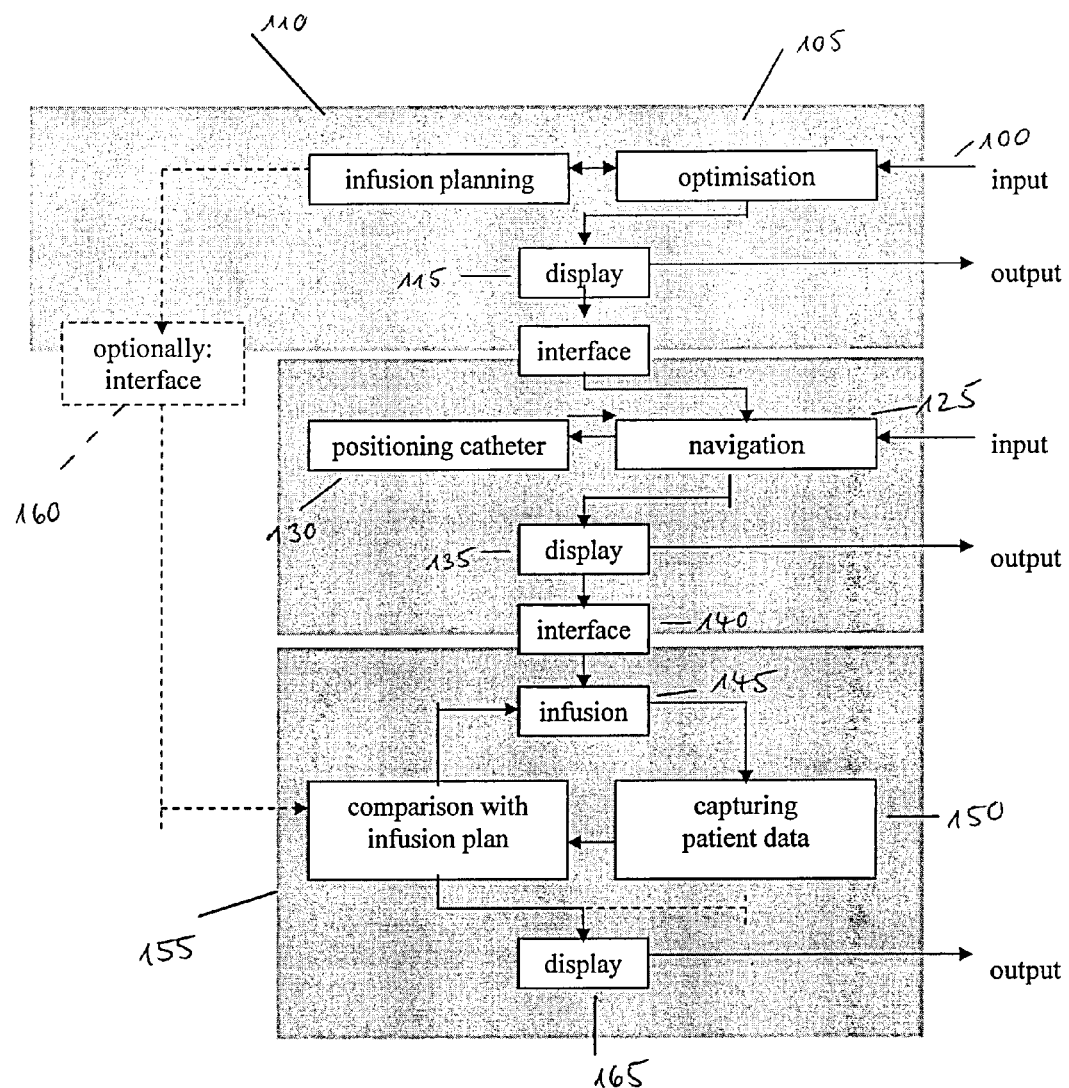
FIG. 1 is a flow diagram of an exemplary method for planning and performing an infusion in accordance with the invention.

The present invention provides a system and method that utilizes knowledge about infusion processes in tissue, particularly in brain tissue. Once the target area is defined, the system and method suggests an optimal infusion procedure in terms of a number of catheters to be used, positioning of the respective catheters, convection or infusion parameters, such as flow rate, catheter radius and/or infusion time, catheter guidelines or any constraint or condition that may be taken into account that may lead to an optimal target coverage by a substance to be delivered by the respective catheter(s).

In a first approximation, a spherical fluid distribution can be calculated for each catheter tip, wherein backflow of a substance or fluid to be delivered by the respective catheter can be taken into account as described in the corresponding European Patent Application with the title "Method and Apparatus for infusing substances". An algorithm can be developed and integrated into a software application that calculates and displays the positioning of such spheres, such that the outlined target region is covered.

The system and method uses the concept that the distribution of a fluid or substance to be infused into tissue is basically distributed along spheres or cylinders. This concept provides good coverage of the area to be treated, as one or more spheres or cylinders can be constructed or simulated around delivery devices, such as catheters. The spheres or cylinders each can have a different radius depending on the infusion plan if, for example, the delivery of a fluid through a first catheter is started prior to the delivery through a second or subsequent catheter.

Further assumptions can be made, such as safety margins that might be set so that the overlap of spheres or cylinders, for example, can be determined. Additionally, the diameter of the spheres or cylinders can be manually adjusted or can be adjusted based on convection parameters such as flow rate, infusion time, pressure and catheter radius. Risk structures can be outlined automatically or manually and can be rated, wherein the overlap of fluid distribution and risk structures can be adjusted. Further, the spheres and trajectories can be adjusted according to catheter placement guidelines.

The design of the infusion process includes information regarding factors such as catheter numbers, selection of infusion parameters (flow rate, pressure head, infusion time), catheter type, position of the catheters, and so on. Traditionally, the physician establishes the infusion process without direct software support. Known methods such as the use of catheter guidelines support physicians for an optimal coverage. These guidelines, however, are based on general rules that are independent of arbitrary target volume and shape, so that these catheter guidelines have limited applicability for an individually shaped infusion process. Furthermore, existing methods based on simulation of the infusate transport provide information about the distribution of the fluid in tissue, and the physician can modify catheter placement planning when considering simulation predictions. This approach demands input information, such as flow rate, infusion time, catheter radius and catheter positioning, be provided by the user and, thus, the approach does not directly support the user in providing an improved infusion set-up (e.g., by suggesting appropriate locations for catheter positions, flow rate, catheter type, . . . ) but merely delivers information about an existing set-up that can then be refined by the user according to the delivered information.

In contrast, the system and method described herein provides extended support for catheter placement. Beyond simulation prediction, the system and method provide information regarding the optimal infusion process design that satisfies user demands. These demands can be the target volume as well as the number of catheters, catheter type, infusion parameters and any requirement that the user considers important for an optimal infusion. As a result, the user obtains global information not only regarding the simulated fluid predictions, but also on the optimal infusion process itself. Conventional methods do not directly support the physician in establishing the most adequate infusion process.

The system and method for preparing and assisting an infusion, and in particular optimally positioning at least one catheter, may be used for interstitial infusion. This can enable optimal infusions to be executed while using a minimal number of catheters. In general, it is preferable to infuse a maximum amount of fluid with a minimum number of operations or catheter injections, such that minimally invasive operations can be executed that reduce or minimize side effects, and possible treatment hazards for the patient can be largely excluded.

The method relates to arranging at least one catheter on a body, in particular on a head, wherein the individual anatomical structure and, in particular, the tissue structure are determined body-specifically. Furthermore, the position of the interstitial fluid, in particular the position relative to the surrounding tissue or body structures, the amount of fluid, and the distribution of the fluid, can be determined body-specifically. In general, it is advantageous to determine all the parameters that influence how the infused fluid proceeds, such as for example the type or composition of the fluid, the pressure distribution, or other parameters. Imaging methods, such as, for example, nuclear magnetic resonance (MRI) methods, computer tomography (CT) methods, ultrasound methods, X-ray methods, SPECT methods, PET methods or other suitable methods can be used to determine the above-mentioned data and information. Advantageously, other examinations or measurements also can be performed to determine, for example, a pressure or a pressure distribution of the interstitial fluid or the composition of said infused fluid. The body-specific or head-specific information obtained in this way can be evaluated and, on the basis of the evaluation, it can be determined how to optimally position one or more catheters. To this end, one or more suitable positions for catheters can be predetermined, for example in a body coordinate system or in a system-specific coordinate system, at which positions one or more catheters can be positioned simultaneously or sequentially, to perform an optimal infusion.

The system and method also relates to simulating fluid infusion through a catheter in a body, in particular in the interstice, wherein anatomical data on the structure of the body and/or the tissue may be individually and body-specifically determined as described herein. The position, amount, distribution and/or type of interstitial fluid or tissue can be determined body-specifically, wherein it can be assumed that one or more catheters are positioned simultaneously or sequentially at one or more predetermined locations. From this information, the course of infusion, in particular the infusion of fluid into the body, can be simulated in order to find suitable positions for attaching one or more catheters or to verify their effectiveness.

Using a simulation, other infusion parameters also may be determined, optimized or verified, such as for example a flow rate, a positive pressure present on the catheter, catheter geometry, or the like. The simulation procedure can be performed on the assumption that the catheters are positioned on the body as described herein.

The catheter/s can be advantageously moved to the desired position on the body using known navigation methods. To this end, active or passive markers, such as for example reflective surfaces, can be attached to the catheter.

Preferably, parameters influencing the infusion of the fluid, such as, for example, the flow characteristics of a particular fluid, can be determined in a specific type of tissue and used to determine the optimal position of a catheter and/or for a simulation. Such body-specific parameters, for example, can be stored in a database and determined by examination, before the method is performed.

Parameters describing the properties of the fluid to be infused may likewise be provided in a database and, for example, can be used to plan the arrangement of a catheter or to simulate infusing the fluid. The viscosity, the interaction between a particular fluid and a particular tissue, the flow characteristics in a particular type of tissue, or other information can be stored in a database so as to be able to perform the methods described herein.

Preferably, the methods are performed using a database containing information and parameters for one or more different types of available catheters. For example, the database may include data on the geometry, in particular the diameter, of the catheter, the material, the surface and its properties when interacting with tissue or fluids to be drained, wherein one or more catheters can be selected automatically and/or by an manually (e.g., by an operator).

Information on possible advantageous ways of adapting, changing or processing the catheters that are to be used can be determined and output by the method so as to arrange at least one catheter on a body. For example, an optimal catheter length can be determined such that a standardized catheter to be used with the method can be cut to a desired length or modified in some other way.

Preferably, other parameters influencing infusion can be determined, such as a positive pressure to be applied to a catheter, which can be used to further optimize the infusion. In this way, the infusion rate of the fluid, usually in the range of a few ml/h, can be influenced and regulated.

Advantageously, a verification method can be performed. For example, further data can be captured intra-operatively using an imaging method or other measurement, in order to determine the body-specific structures changed by the infusion and/or the position, distribution and amount of the fluid after partial or complete infusion. On the one hand, this information can be used to verify an executed infusion and also, on the other hand, to correct or reposition one or more catheters, as may be necessary, to replace catheters, to change the flow rate or to influence other parameters relevant to infusion. This can be done to take into account, for the further course of the infusion, the fact that an already reduced pressure or infused fluid may cause a change in the position of a body or tissue structure and that the infusion plan may have to be changed, for example, by repositioning a catheter or changing parameters.

The system and method described herein also relates to controlling infusion, wherein a substance can be introduced into a body, for example by means of one or more catheters, at at least one location on said body. A pressure or negative pressure can be applied to the body at at least one other location, in particular at a region of the body or interior of the body, such that the distribution of a substance introduced into the body at at least one location can be influenced by applying a pressure or a negative pressure to other locations on the body. It is thus possible to establish preferred flow or spreading directions for an infused substance, in order to introduce said substance as precisely as possible into particular regions of the body. Furthermore, applying a negative pressure can reduce or remove a possibly damaging internal pressure in the body, which would be further increased by introducing a substance. To apply a negative pressure, catheters can be positioned in the interstice or in the ventricles in order to apply a negative pressure at at least one desired location on the body and to influence the distribution or flow direction of a substance introduced into the body, for example.

In general, the method for controlling infusion can be used in combination with one or more of the method steps described herein. For example, based on body-specific anatomical and/or tissue structure data, the catheters can be suitably positioned to introduce a substance and/or to apply a positive pressure or a negative pressure, and an infusion process can be simulated to determine the distribution of a substance in the body. Furthermore, the catheters can be positioned using navigation methods. It is also possible to use information stored in databases to plan or perform the method as described above.

The method may be embodied as a computer program which can be loaded into the memory of a computer and which includes sections of software code. The software code can implement one or more steps of the methods described herein when the program is run on a computer. The computer program may be embodied as a computer program product stored on a computer-compatible medium or data carrier.

A device for simulating fluid infusion into a body can include a data capture device for capturing structural data of the body and/or the position of a fluid in a body, such as for example a nuclear spin tomograph and a computer system for determining the arrangement of at least one catheter on a body. The device can further include an input device for inputting the position of at least one catheter in order to simulate the fluid infusion from the body, using the body-specific and fluid-related data determined by the data capture device.

In general, the device can be used to implement one or more of the method steps described herein. To this end, databases can be provided for storing parameters or characteristics of one or more catheters, particular body parameters, fluid parameters and/or infusion parameters.

In order to perform the infusion, a device for setting the infusion flow rate, such as for example a pump, can be provided, wherein the pump is operable to generate a desired positive pressure in order to perform infusion as planned and/or simulated by the methods described herein.

Known methods using markers, such as for example the VectorVision system distributed by the assignee of the present application, can be used to navigate one or more catheters in order to ensure that said catheters are optimally positioned and seated.

With respect to a device and methods for administering a substance, which may be used in combination with the invention, reference is made to European patent application No. 01 128 614.3, filed by the Applicant on Nov. 30, 2001, the contents of which are hereby incorporated by reference its entirety.

FIG. 1 shows a schematic flow chart for preparing and performing an exemplary infusion in accordance with the invention. As shown in FIG. 1, patient data are input at step 100, for example by a nuclear spin tomograph. The patient data are used to determine one or more particular regions for positioning catheters for infusion, and to plan the infusion to be performed. The data can be obtained, for example, using the nuclear spin resonance system 300 as shown schematically in FIG. 3, to examine the patient. Using parameters for the properties of the tissue structures and for various types of catheters, stored for example in databases, one or more catheters suitable for the infusion can be selected, once the exact position of the target area to be treated by infusion and of the body or tissue structure has been determined.

The parameters of the body or the patient, obtained for example using the nuclear spin resonance method, can be used together with the catheter parameters and the fluid parameters, also for example stored in databases, to plan the infusion. In this way, the course of the infusion to be performed can be planned and optimized as indicated at blocks 105 and 110, by balancing the conditions of infusing as great a proportion of the fluid as possible into the body structure or the target tissue, while doing so in as few operations as possible. In general, as few catheters or needles should be positioned as possible, said catheters or needles being supplied through as few access points as possible. This optimized planning of the infusion is output via a display at step 115, such that for example a two-dimensional or three-dimensional representation can be output by imaging various incision planes, in order to display the resultant infusion plan.

Figure 3:
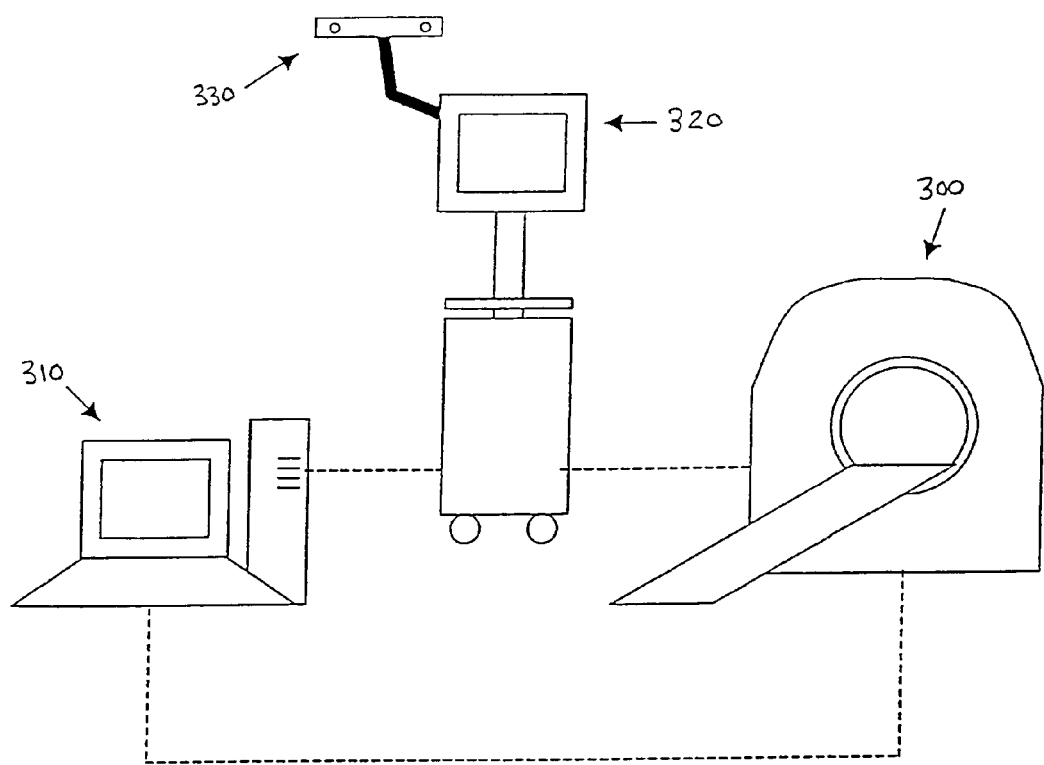
FIG. 3 is a schematic diagram of an exemplary system for planning and performing an infusion in accordance with the invention.

The infusion plan produced in this manner can be transmitted via an interface at step 117 and received by a navigation system at step 125, such as for example the VectorVision system 320 shown schematically in FIG. 3, in order to position the selected catheter or catheters at the predetermined locations on the body, based on the planning data, as indicated at step 130. The catheters can be positioned automatically, for example using a robot, or by hand if guided by the navigation system, wherein a display device can indicate whether a catheter has been positioned correctly or whether it still has to be moved in a particular direction. The data can be displayed as indicated at block 135, and then transferred via an interface at step 140.

Once the catheter or catheters have been successfully positioned, the actual infusion is performed at step 145 using the infusion parameters predetermined by the plan, such as for example a flow rate which is constant or which changes with time. To this end, patient data are again captured at step 150 to determine the actual distribution of the fluid in the body or tissue. Using the parameters predetermined by the plan and the infusion simulation results based on them, a comparison is made at step 155. The comparison can be between the actual infusion data, in particular the distribution of the partially infused fluid, and the predetermined distribution of fluid. Based on the comparison, appropriate parameters can be altered, such as for example the flow rate, the infusion amount or a pressure or suction applied to the catheter for performing infusion. Preferably, the alterations take into account known active mechanisms in order to obtain the desired, planned infusion result. Again, the actual distribution of the interstitial fluid measured can be output together with any deviations and correction methods via a display, for example to enable an operator to intercede in the infusion method manually.

Figure 2:
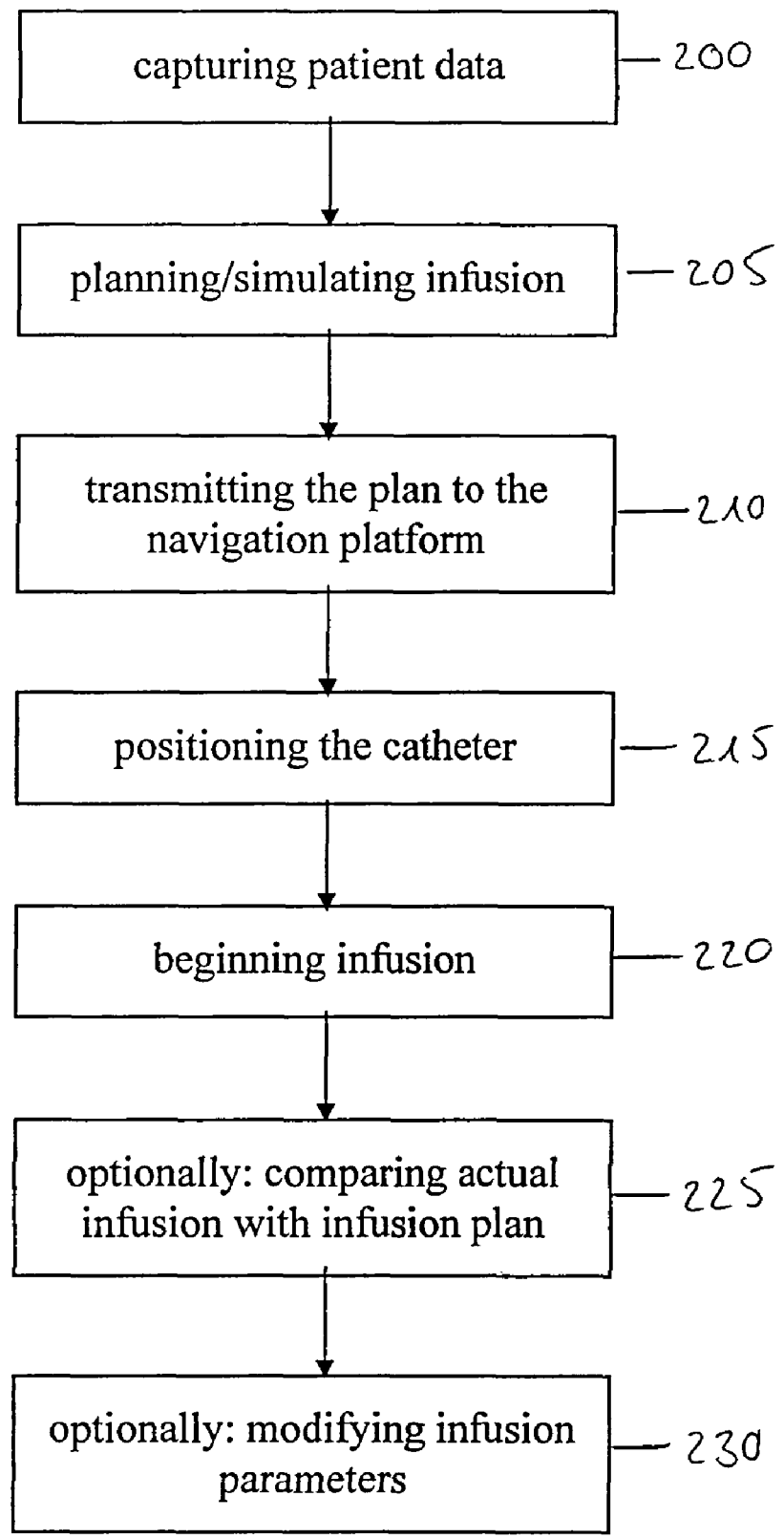
FIG. 2 is a simplified flow diagram of an exemplary infusion performed in accordance with the invention.

FIG. 2 schematically shows a simplified sequence of exemplary planning and performing infusion in accordance with the invention. Firstly, patient data are captured at step 200 using a diagnostic imaging method, such as for example a nuclear spin resonance method, to obtain the current patient parameters. The current patient parameters can include, for example, tissue density, pressure and position of a fluid to be drained. Using the patient parameters determined in this way, as well as catheter and infusion parameters obtained from a database and/or predetermined for a specific infusion, the infusion is planned and/or simulated at step 205. Based on the parameter data determined in this way, the infusion plan is transmitted to a navigation platform at step 210, by which the catheter or catheters are to be positioned on the patient as provided for in the infusion plan at step 215. At step 220, infusion begins once the catheters have been positioned and is performed using the planned and as appropriate simulated parameters. At step 225, a comparison can be made between the infusion actually performed and the infusion plan and, in the event of deviations, the corresponding parameters can be modified at step 230, preferably by utilizing known active mechanisms.

FIG. 3 schematically shows an exemplary system which may be used to plan and perform an infusion in accordance with the invention. Patient data can be obtained in a nuclear spin tomograph 300 and transmitted to a planning system 310 and to a navigation system 320. Using the navigation system 320, the catheter or catheters can be positioned at a desired location on the body using, for example, known reflectors or markers attached to one or more of the catheters, positional data of the markers being captured by infrared cameras 330. The planning system 310 can determine the suitable catheter parameters and infusion parameters for a predetermined infusion to be performed, using the patient parameters determined by the nuclear spin resonance system 300, in order to perform the infusion.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of adjusting infusion parameters that provide coverage of a selected target volume for direct infusions of a fluid, comprising:
   obtaining image data corresponding to a patient's anatomical structure;
   selecting, based on the image data, a target volume that is to receive the fluid;
   developing an infusion plan for infusing the fluid into the target volume; and
   based on the plan, calculating, using a microprocessor, an optimal packing of spheres or cylinders in the selected target volume to determine the coverage of the fluid in the selected target volume.

2. The method of claim 1, wherein the fluid is at least one of a drug, diluted cells, viral vectors, molecules, diluted microspheres, or diluted micelles.

3. The method of claim 1, wherein spheres or cylinders refer to a geometrical shape of the fluid distribution.

4. The method of claim 3, further comprising calculating the geometrical shape of the fluid distribution based on convection related parameters.

5. The method of claim 4, wherein calculating the geometrical shape includes using at least one of flow rate, pressure head, infusion time, catheter radius, catheter type, tissue properties as the convention related parameters.

6. The method of claim 3, further comprising calculating the geometrical shape of the fluid distribution based on diffusion related parameters.

7. The method of claim 6, wherein calculating the geometrical shape includes using at least one of time, diffusivity, infusion time, concentration gradients, catheter radius, infusate properties, catheter type, catheter number, tissue properties as the diffusion related properties.

8. The method of claim 1, wherein the infusion parameters include at least one of a flow rate, pressure, infusion time, catheter types and/or catheter diameters, a number of catheters used to perform the infusion, a position of a catheter trajectory and/or a position of a catheter tip, or include or take into consideration catheter placement guidelines for at least one catheter.

9. The method of claim 1, further comprising manually adjusting at least one of the parameters for at least one catheter.

10. The method of claim 1, further comprising automatically calculating at least one of the parameters for at least one catheters.

11. The method of claim 1, further comprising acquiring from external sources at least one of the parameters for at least one catheter.

12. The method of claim 11, wherein acquiring includes using software, literature or a user as an external source.

13. The method of claim 1, further comprising interactively removing at least one catheter and automatically updating the coverage of the selected target volume to reflect the removal.

14. The method of claim 1, further comprising interactively removing and/or changing at least one parameter and automatically updating the selected target volume to reflect the removal or change.

15. The method of claim 1, further comprising manually or automatically outlining the target volume.

16. The method of claim 15, further comprising rating at least one outlined target volume in terms of importance of its coverage or in terms of importance of avoidance of its coverage.

17. The method of claim 1, further comprising rating the target volume in terms of risk structures.

18. The method of claim 1, further comprising adjusting a demanded overlap between the target volume and a calculated infusion area.

19. The method of claim 1, further comprising adjusting a demanded overlap between the target volume and a calculated non-infusion area.

20. The method of claim 1, further comprising adjusting an overlap between infusion results from different catheters.

21. The method of claim 20, wherein adjusting the overlap includes adjusting the overlap in terms of maximum concentration threshold.

22. The method of claim 1, further comprising adjusting the fluid distribution in the target volume in terms of therapeutic effects.

23. The method of claim 1, further comprising using at least part of the determined coverage to refine the plan for placement of intra-cranial catheters.

24. The method of claim 23, wherein using at least part of the determined coverage includes automatically or manually refining the plan.

25. A non-transitory computer readable storage medium with an executable program stored thereon for adjusting infusion parameters that provide coverage of a selected target volume for direct infusions of a fluid, wherein the program instructs a processor to calculate an optimal packing of spheres or cylinders in the selected target volume to determine the coverage of the selected target volume.

26. A system for adjusting infusion parameters that provide coverage of a selected target volume in tissue for direct infusion of a fluid, comprising:
an imaging device for obtaining image data;
a processor operatively coupled to the imaging device and configured to obtain patient-specific medical and/or anatomical image data from the imaging device;
a data bank operatively coupled to the processor and including information for calculating infusion relevant parameters from the imaging data obtained from the imaging device; and
an infusion system including at least one delivery device and at least one injecting mechanism, said injecting mechanism controllable by the processor based on the information obtained from the imaging device and/or the data bank so as to cover the target volume with a substance delivered or infused by the at least one delivery device, wherein said infusion system is configured to determine the coverage of the selected target volume by the substance by calculating an optimal packing of spheres or cylinders in the selected target volume.

27. A device for planning an infusion of a substance into a target volume, comprising:
a first input for receiving infusion parameters for the target volume;
a second input for receiving patient specific data pertaining to the target volume;
a processor and memory; and
computer executable instructions stored in memory and executable by the processor, wherein when executed by the processor, the computer executable instructions cause the processor to use the infusion parameters and patient specific data to determine a coverage of the substance in the target volume by calculating an optimal packing of spheres or cylinders in the target volume.

28. The device according to claim 27, wherein each sphere or cylinder corresponds to a respective infusion device or placement of an infusion device in the target volume.

* * * * *